(12) United States Patent
Chou et al.

(10) Patent No.: US 10,416,071 B2
(45) Date of Patent: Sep. 17, 2019

(54) CORROSION DETECTION CIRCUIT FOR CIRCUIT BOARD AND MOTOR DRIVE HAVING THE SAME

(71) Applicant: FANUC CORPORATION, Yamanashi (JP)

(72) Inventors: Norihiro Chou, Yamanashi (JP); Kiichi Inaba, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 82 days.

(21) Appl. No.: 15/153,812

(22) Filed: May 13, 2016

(65) Prior Publication Data

US 2016/0356698 A1 Dec. 8, 2016

(30) Foreign Application Priority Data

Jun. 4, 2015 (JP) .................................. 2015-114231

(51) Int. Cl.
*G01N 17/00* (2006.01)
*G01N 17/04* (2006.01)

(52) U.S. Cl.
CPC ........... *G01N 17/006* (2013.01); *G01N 17/04* (2013.01)

(58) Field of Classification Search
CPC ...... G01N 17/00; G01N 17/006; G01N 17/02; G01N 17/04; G01N 17/043; G01N 17/046; G01R 27/14
USPC ............... 204/404, 400; 324/71.2, 700, 693; 436/6; 73/86; 702/34; 205/775.5, 776.5, 205/777
See application file for complete search history.

(56) References Cited

U.S. PATENT DOCUMENTS

| | | | | | |
|---|---|---|---|---|---|
| 3,067,386 | A | * | 12/1962 | Freedman | ............... C23F 13/04 324/700 |
| 4,267,148 | A | * | 5/1981 | Dickson | ................. G01N 17/00 422/53 |

(Continued)

FOREIGN PATENT DOCUMENTS

| CN | 101571561 A | 11/2009 |
|---|---|---|
| CN | 101763905 A | 6/2010 |

(Continued)

OTHER PUBLICATIONS

Untranslated Decision to Grant a Patent mailed by Japan Patent Office (JPO) for Application No. JP 2015-114231, dated Apr. 25, 2017, 3 pages.

(Continued)

*Primary Examiner* — Jeff W Natalini
*Assistant Examiner* — Steven L Yeninas
(74) *Attorney, Agent, or Firm* — Fredrikson & Byron, P.A.

(57) ABSTRACT

A corrosion detection circuit according to an embodiment of the present invention includes an insulating board; a test chip having a corrodible metal, mounted on the surface of the insulating board; a plurality of resistors each having a higher resistance value than the test chip after a change due to an environment including contact with the test chip and the adhesion of dust to the test chip; and a voltage detection circuit for detecting the output voltage of a divided voltage output point, when a voltage is applied to the test chip and a voltage dividing circuit using the plurality of resistors. The voltage detection circuit detects a break in the test chip by corrosion based on a variation in the output voltage.

7 Claims, 11 Drawing Sheets

(56) References Cited

U.S. PATENT DOCUMENTS

| | | | | |
|---|---|---|---|---|
| 4,338,563 | A | * | 7/1982 | Rhoades ............... G01N 27/046 324/700 |
| 5,243,297 | A | * | 9/1993 | Perkins ................. G01N 17/00 204/404 |
| 6,936,158 | B2 | * | 8/2005 | Nielsen .................... G01B 7/06 204/404 |
| 6,946,855 | B1 | * | 9/2005 | Hemblade ............. G01N 17/04 324/700 |
| 7,109,721 | B2 | * | 9/2006 | Maurer .................. H01H 1/605 307/137 |
| 2004/0130340 | A1 | * | 7/2004 | Tiefnig .................. G01N 17/00 324/700 |
| 2005/0029096 | A1 | | 2/2005 | Maurer et al. |
| 2005/0263395 | A1 | | 12/2005 | Nielsen et al. |
| 2007/0193887 | A1 | | 8/2007 | Tormoen et al. |
| 2008/0179198 | A1 | * | 7/2008 | Burgess ................. G01N 17/02 205/775.5 |
| 2012/0038377 | A1 | | 2/2012 | Hamann et al. |

FOREIGN PATENT DOCUMENTS

| | | |
|---|---|---|
| CN | 102749360 A | 10/2012 |
| CN | 203025316 U | 6/2013 |
| CN | 205809241 U | 12/2016 |
| GB | 2352520 A | 1/2001 |
| JP | 10300699 A | 11/1998 |
| JP | 2005109084 A | 4/2005 |
| JP | 2005257532 A | 9/2005 |
| JP | 2006292460 A | 10/2006 |
| JP | 2009216391 A | 9/2009 |
| JP | 2010156661 A | 7/2010 |
| JP | 2014153089 A | 8/2014 |

OTHER PUBLICATIONS

English machine translation of Decision to Grant a Patent mailed by Japan Patent Office (JPO) for Application No. JP 2015-114231, dated Apr. 25, 2017, 3 pages.

English Abstract and Machine Translation for Japanese Publication No. 10-300699, published Nov. 13, 1998, 10 pgs.

English Abstract and Machine Translation for Japanese Publication No. 2009-216391, published Sep. 24, 2009, 16 pgs.

English Abstract for Japanese Publication No. 2014-153089 A, published Aug. 25, 2014, 1 pg.

English Abstract for Japanese Publication No. 2010-156661 A, published Jul. 15, 2010, 1 pg.

English Abstract for Japanese Publication No. 2006292460 A, published Oct. 26, 2006, 1 pg.

English Abstract for Japanese Publication No. 2005257532 A, published Sep. 22, 2005, 1 pg.

English Abstract for Japanese Publication No. 2005109084 A, published Apr. 21, 2005, 1 pg.

English Abstract and Machine Translation for Chinese Publication No. 205809241 U, published Dec. 14, 2016, 9 pgs.

English Abstract and Machine Translation for Chinese Publication No. 101571561 A, published Nov. 4, 2009, 9 pgs.

English Abstract for Chinese Publication No. 203025316 U, published Jun. 26, 2013, 1 pg.

English Abstract and Machine Translation for Chinese Publication No. 102749360 A, published Oct. 24, 2012, 8 pgs.

English Abstract and Machine Translation for Chinese Publication No. 101763905 A, published Jun. 30, 2010, 7 pgs.

\* cited by examiner

CORROSION DETECTION CIRCUIT FOR CIRCUIT BOARD AND MOTOR DRIVE HAVING THE SAME

BACKGROUND OF THE INVENTION

1. Field of the Invention

The present invention relates to a corrosion detection circuit for a circuit board and a motor drive having the corrosion detection circuit, and more specifically relates to a corrosion detection circuit that includes a test chip having a corrodible metal, resistors having high resistance values, and a voltage detection circuit to enable the detection of the risk of corrosion by a corrosive liquid or gas in advance without applying a specific coating material or forming a specific resist, and a motor drive having the corrosion detection circuit.

2. Description of Related Art

Motor drives have the problem that cutting fluids, cleaning fluids, and other liquids and gases used in factories cause corrosion of electronic components and circuit boards, thus impairing necessary functions. As a measure against the problem, there is a method in which a test chip having a corrodible metal is arranged on the circuit boards and the resistance value thereof is monitored to issue an alarm before impairing the functions of the circuits. However, this method may detect a variation in the resistance value due to environmental factors such as a finger contacting the test chip or the adhesion of dust to the test chip. It is not necessary to detect such a variation in the resistance value for the motor drives.

As a diagnosis device for a circuit board having an electronic component thereon to solve the above problem, there is known an environment diagnosis device for electrical equipment in which a detection conductive material of a test chip is covered with a silicone coating material having water absorbability and gas permeability to prevent the adhesion of dust to the detection conductive material and a finger contact therewith (for example, Japanese Unexamined Patent Publication (Kokai) No. 10-300699, hereinafter referred to as "patent literature 1").

A malfunction detection circuit in which a sub pattern, which is wired in a part of a circuit board as a circuit for detecting a break in a wiring pattern formed on the circuit board due to corrosion and a short in the wiring pattern due to migration to detect a malfunction in the circuit board, is covered with a sub resist that is thinner than the thickness of a solder resist for covering the other portions is known. The sub pattern has traces arranged in parallel at predetermined intervals (for example, Japanese Unexamined Patent Publication (Kokai) No. 2009-216391, hereinafter referred to as "patent literature 2").

SUMMARY OF THE INVENTION

In the conventional techniques described in the patent literatures 1 and 2, the above problem is solved by means of applying the specific coating material or forming the specific resist. However, the application of the coating material or the formation of the specific resist causes other problems such as requiring specific processing steps, technical difficulty, and cost increase, etc.

A corrosion detection circuit according to an embodiment of the present invention includes an insulating board; a test chip having a corrodible metal, mounted on the surface of the insulating board; a plurality of resistors each having a higher resistance value than the test chip after a change due to environmental factors including contact with the test chip or the adhesion of dust to the test chip; and a voltage detection circuit for detecting the output voltage of a divided voltage output point, when a voltage is applied to the test chip and a voltage dividing circuit using the plurality of resistors. The voltage detection circuit detects a break in the test chip by corrosion based on a variation in the output voltage.

BRIEF DESCRIPTION OF THE DRAWINGS

The objects, features, and advantages of the present invention will be more apparent from the following description of embodiments in conjunction with the attached drawings, wherein.

DETAILED DESCRIPTION OF THE INVENTION

A corrosion detection circuit according to the present invention will be described below with reference to the drawings.

First Embodiment

Figure 1:
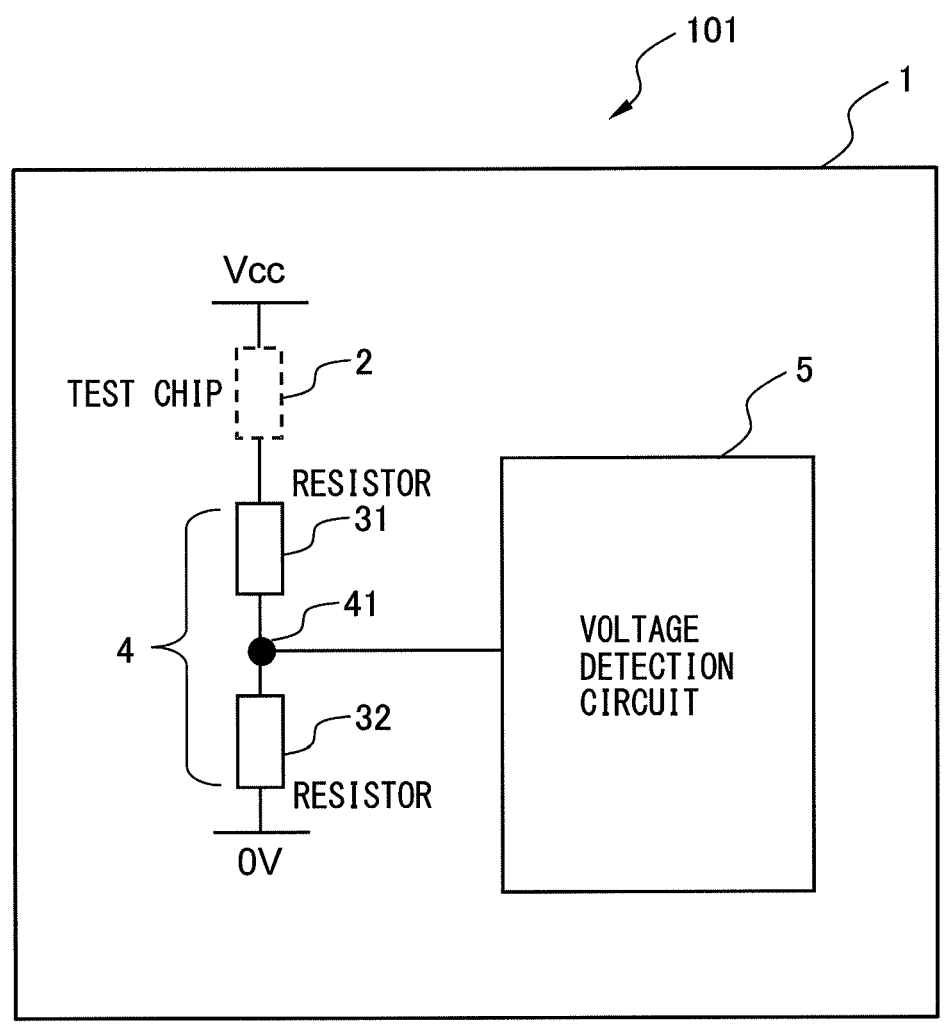
FIG. 1 is a block diagram of a corrosion detection circuit according to a first embodiment of the present invention.

A corrosion detection circuit according to a first embodiment of the present invention will be described. FIG. 1 is a block diagram of the corrosion detection circuit according to the first embodiment of the present invention. A corrosion detection circuit 101 according to the first embodiment of the present invention includes an insulating board 1, a test chip 2 that is mounted on the surface of the insulating board 1 and has a corrodible metal, a plurality of resistors 31 and 32 having higher resistance values than the test chip 2 after a change due to environmental factors including contact with the test chip 2 or the adhesion of dust to the test chip 2, and a voltage detection circuit 5 for detecting the output voltage of a divided voltage output point 41 when a voltage is applied to the test chip 2 and a voltage dividing circuit 4 using the plurality of resistors 31 and 32. The voltage detection circuit 5 detects a break in the test chip 2 due to corrosion, based on a variation in the output voltage.

Figure 2:
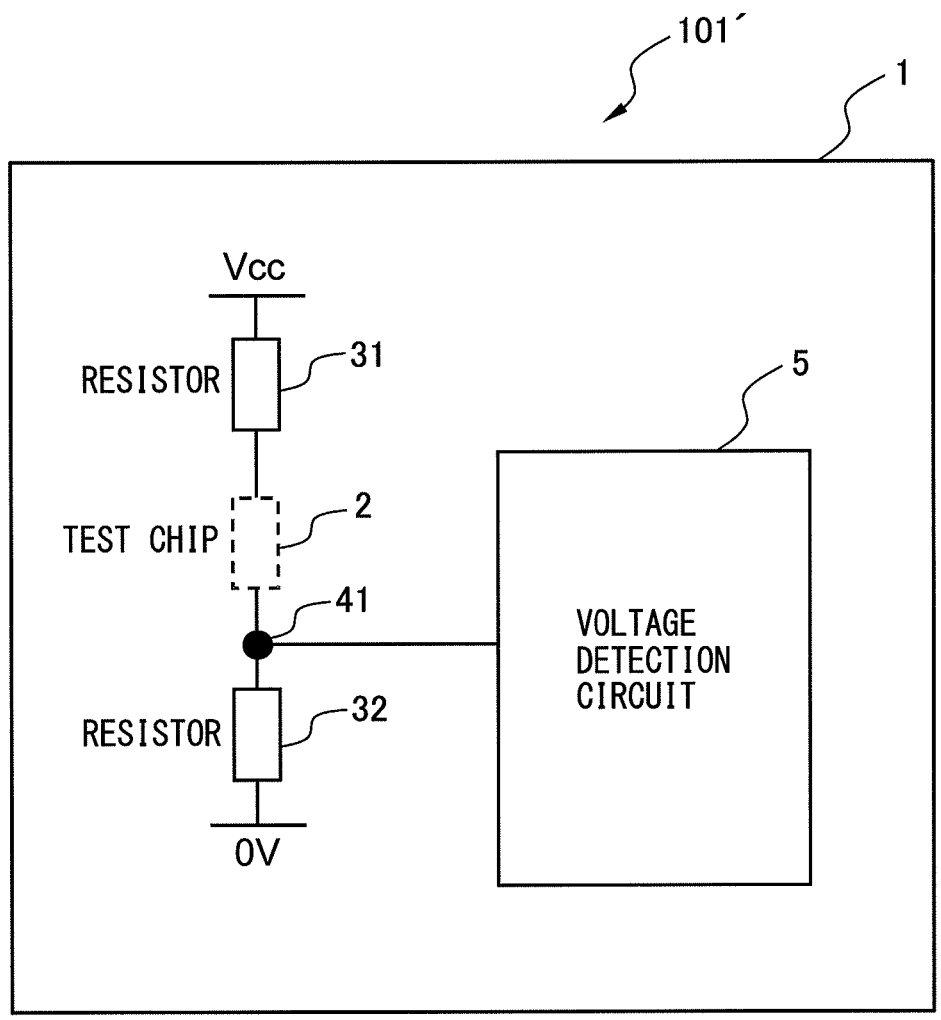
FIG. 2 is a block diagram of a modification example of the corrosion detection circuit according to the first embodiment of the present invention.

As shown in FIG. 1, the test chip 2 having the corrodible metal (silver, copper, or the like) is mounted on the insulating board 1 in series to the voltage dividing circuit 4 including the resistors 31 and 32. A voltage $V_{cc}$ is applied to the series circuit that includes the test chip 2 and the voltage dividing circuit 4. It is noted that the resistors 31, 32 and the test chip 2 are able to be arranged in random order from the divided voltage output point 41 of the voltage dividing circuit 4 to a power supply $V_{cc}$ or a ground (0 [V]), between the divided voltage output point 41 and the power supply $V_{cc}$ or between the divided voltage output point 41 and the ground. By way of example, FIG. 2 shows the configuration of a modification example (101') of the corrosion detection circuit according to the first embodiment of the present invention. As shown in FIG. 2, the order of the resistor 31 and the test chip 2 may differ from that shown in FIG. 1 between the divided voltage output point 41 of the voltage dividing circuit 4 and the power supply $V_{cc}$.

Figure 3:
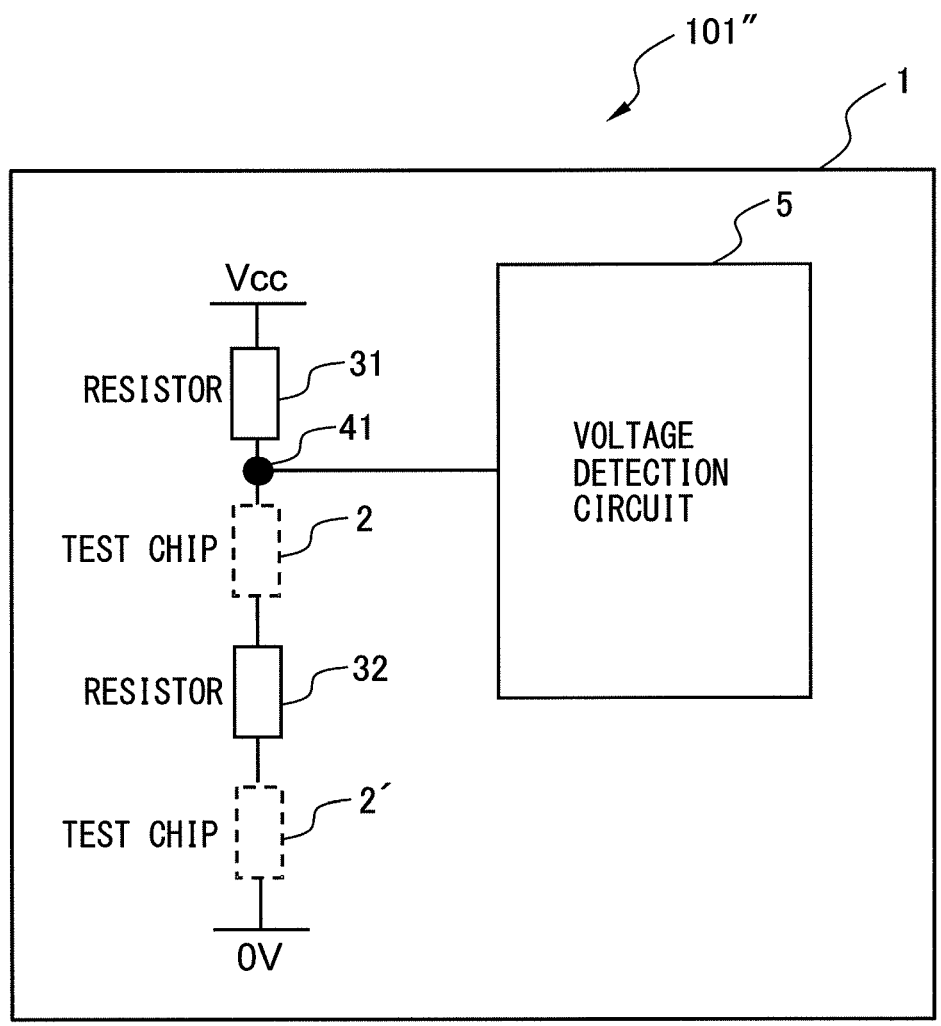
FIG. 3 is a block diagram of another modification example of the corrosion detection circuit according to the first embodiment of the present invention.

In FIG. 1, the test chip 2 may be situated on either of the upper and lower sides of the voltage dividing circuit 4. In other words, the test chip 2 may be arranged on a high voltage side or a low voltage side relative to the divided voltage output point 41. FIG. 1 shows an example in which the test chip 2 is arranged on the high voltage side. FIG. 1 shows the example of the single test chip 2, but the present invention is not limited to this example. That is, a plurality of test chips may be arranged in series. By way of example, FIG. 3 shows the configuration of another modification example (101'') of the corrosion detection circuit according to the first embodiment of the present invention. As shown in FIG. 3, two test chips 2 and 2' may be arranged between the divided voltage output point 41 of the voltage dividing circuit 4 and the ground. It is noted that FIG. 3 shows an example of the two test chips, but the present invention is not limited thereto. That is, three or more test chips may be provided. There is no limitation on the circuit positions of the resistors and the test chips.

Next, the relationship between the presence or absence of corrosion in the test chip 2 and the voltage of the divided voltage output point 41 will be described with reference to FIG. 1. When the test chip 2 does not corrode and has a resistance value sufficiently lower than the resistors 31 and 32 of the voltage dividing circuit 4, the voltage of the divided voltage output point 41 is ($\frac{1}{2}$)$V_{cc}$, provided that the resistors 31 and 32 each have a resistance value of R.

On the other hand, when the test chip 2 is located in a corrosive environment, the corrodible metal may corrode and the test chip 2 is broken. If the test chip 2 is broken, the voltage of the divided voltage output point 41, that is, the output of the voltage dividing circuit 4 increases or decreases. When the test chip 2 is arranged on the high voltage side, as shown in FIG. 1, the break in the test chip 2 decreases the voltage of the divided voltage output point 41 from ($\frac{1}{2}$)$V_{cc}$ to 0 [V]. On the other hand, when the test chip 2 is arranged on the low voltage side, the break in the test chip 2 increases the voltage of the divided voltage output point 41 from ($\frac{1}{2}$)$V_{cc}$ to $V_{cc}$.

Figure 4:
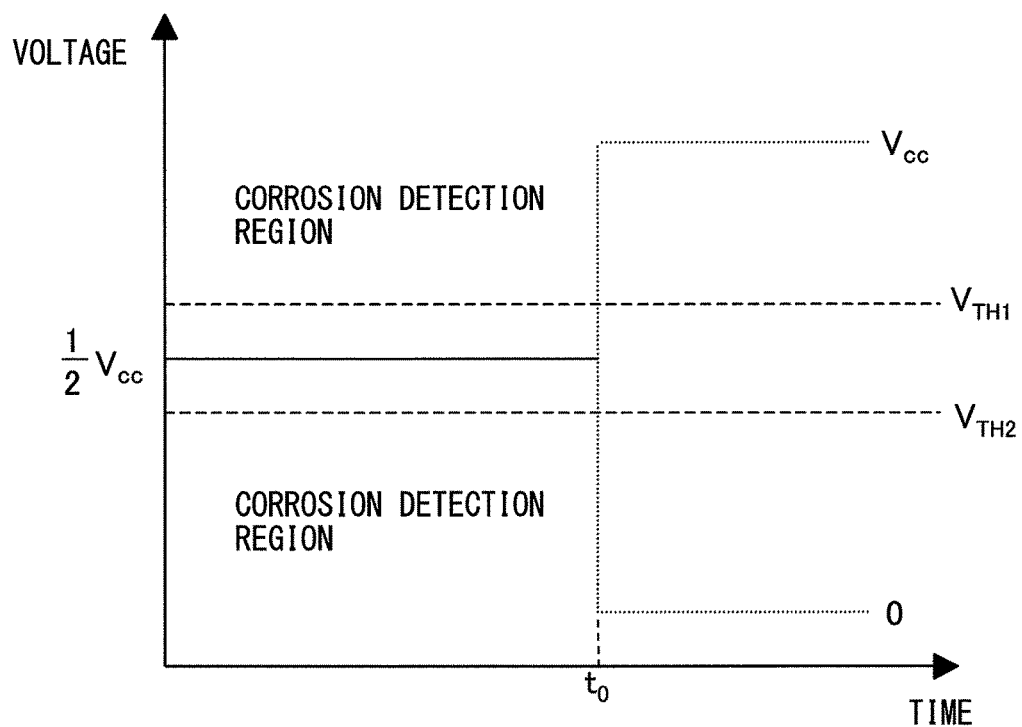
FIG. 4 is a graph showing a temporal variation in the output of a voltage dividing circuit in the corrosion detection circuit according to the first embodiment of the present invention.

FIG. 4 shows a temporal variation in the output of the voltage dividing circuit 4 in the corrosion detection circuit 101 according to the first embodiment of the present invention. Whether the break in the test chip 2 increases or decreases the voltage of the divided voltage output point 41 depends on the position of the test chip 2, as described above. The voltage detection circuit 5 determines that corrosion has occurred by a variation in the voltage out of a range that includes variations in the components and the other margins relative to a normal voltage.

For example, as shown in FIG. 4, it is assumed that a break in the test chip 2 occurs at a time $t_0$. The voltage of the divided voltage output point 41 before the break of the test chip 2 is ($\frac{1}{2}$)$V_{cc}$. When the test chip 2 is arranged on the high voltage side, as shown in FIG. 1, the break in the test chip 2 abruptly decreases the voltage of the divided voltage output point 41 from ($\frac{1}{2}$)$V_{cc}$ to 0 [V] at the time $t_0$. Even before the break in the test chip 2, an environmental change such as contact with the test chip 2 or the adhesion of dust to the test chip 2 is likely to cause a variation in the voltage of the divided voltage output point 41 from ($\frac{1}{2}$)$V_{cc}$. Accordingly, the corrosion detection circuit of the present invention determines that the test chip 2 has been broken, when it is recognized that the voltage of the divided voltage output point 41 has fallen below a predetermined threshold $V_{TH2}$ into a corrosion detection range.

When the test chip 2 is arranged on the low voltage side, in contrast to FIG. 1, the voltage of the divided voltage output point 41 abruptly increases from ($\frac{1}{2}$)$V_{cc}$ to $V_{cc}$ upon the break in the test chip 2 at the time $t_0$. Even before the break in the test chip 2, an environmental change such as contact with the test chip 2 or the adhesion of dust to the test chip 2 is likely to cause a variation in the voltage of the divided voltage output point 41 from ($\frac{1}{2}$)$V_{cc}$. Accordingly, the corrosion detection circuit of the present invention determines that the test chip 2 has been broken, when it is recognized that the voltage of the divided voltage output point 41 has exceeded a predetermined threshold $V_{TH1}$ into a corrosion detection range.

Figure 5:
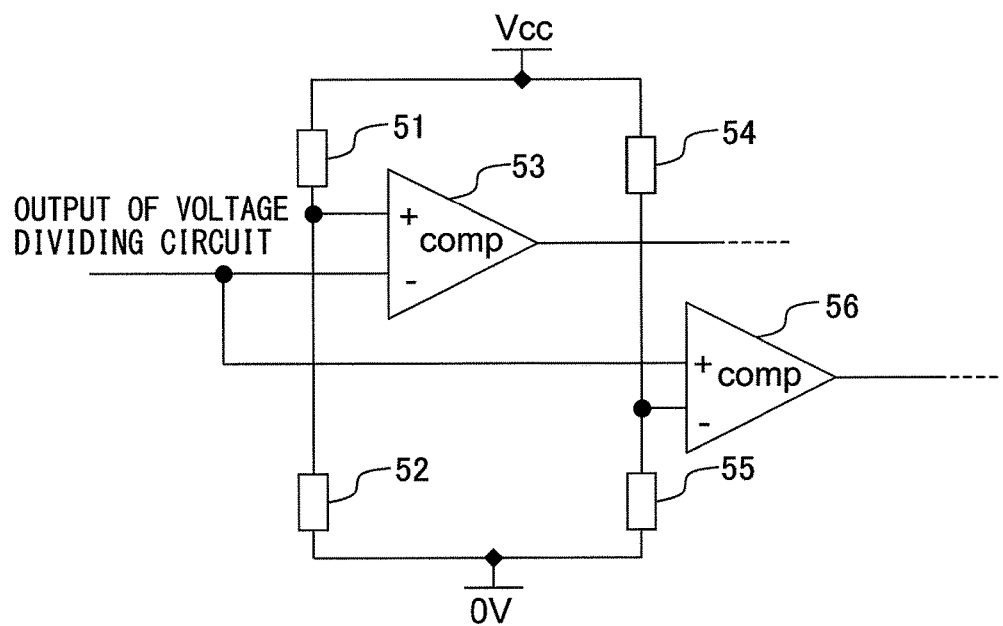
FIG. 5 is a block diagram of an example of a voltage detection circuit in the corrosion detection circuit according to the first embodiment of the present invention.

FIG. 5 shows an example of the voltage detection circuit 5 in the corrosion detection circuit according to the first embodiment of the present invention. There is a case where, for example, the threshold voltage $V_{TH2}$ is inputted to a non-inverting input terminal of a first comparator 53 by dividing the voltage $V_{cc}$ using resistors 51 and 52, while the voltage of the divided voltage output point 41 is inputted to an inverting input terminal thereof. At this time, if the voltage of the divided voltage output point 41 is lower than the threshold voltage $V_{TH2}$, the first comparator 53 outputs a high level so that a break in the test chip 2 is detected. There is also a case where the threshold voltage $V_{TH1}$ is inputted to an inverting input terminal of a second comparator 56 by dividing the voltage $V_{cc}$ using resistors 54 and 55, while the voltage of the divided voltage output point 41 is inputted to a non-inverting input terminal thereof. At this time, if the voltage of the divided voltage output point 41 is higher than the threshold voltage $V_{TH1}$, the second comparator 56 outputs a high level so that a break in the test chip 2 is detected.

Figure 6:
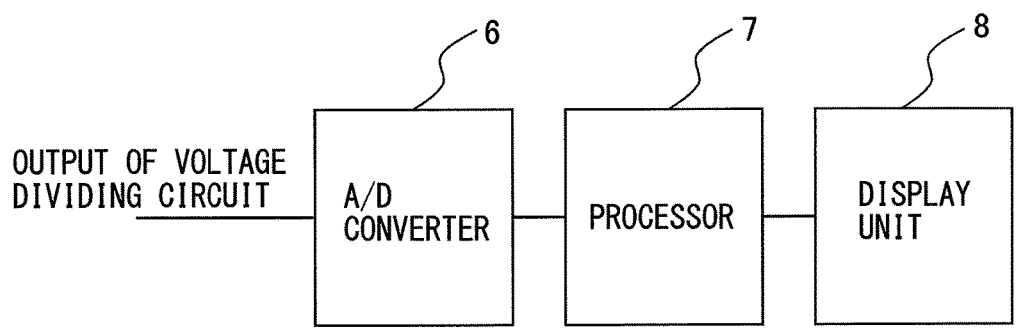
FIG. 6 is a block diagram of another example of the voltage detection circuit in the corrosion detection circuit according to the first embodiment of the present invention.

FIG. 6 shows another example of the voltage detection circuit 5 in the corrosion detection circuit according to the first embodiment of the present invention. FIG. 6 shows an example in which an A/D converter 6 and a processor 7 compose the voltage detection circuit and a display unit 8 is provided ahead. The configuration of FIG. 6 is merely an example, and a configuration having a photocoupler, a configuration having a processor containing an A/D converter, and the like are conceivable. Furthermore, although the display unit 8 is provided ahead of the voltage detection circuit in the example of FIG. 6, a safety circuit or the like may be provided instead.

As described above, according to the corrosion detection circuit of the first embodiment of the present invention, the additionally provided resistors allow variations in a resistance value of the test chip to be subjected to the corrosion, due to disturbances, other than corrosion to be neglected, thus allowing the stable detection of the corrosion.

Second Embodiment

Figure 7:
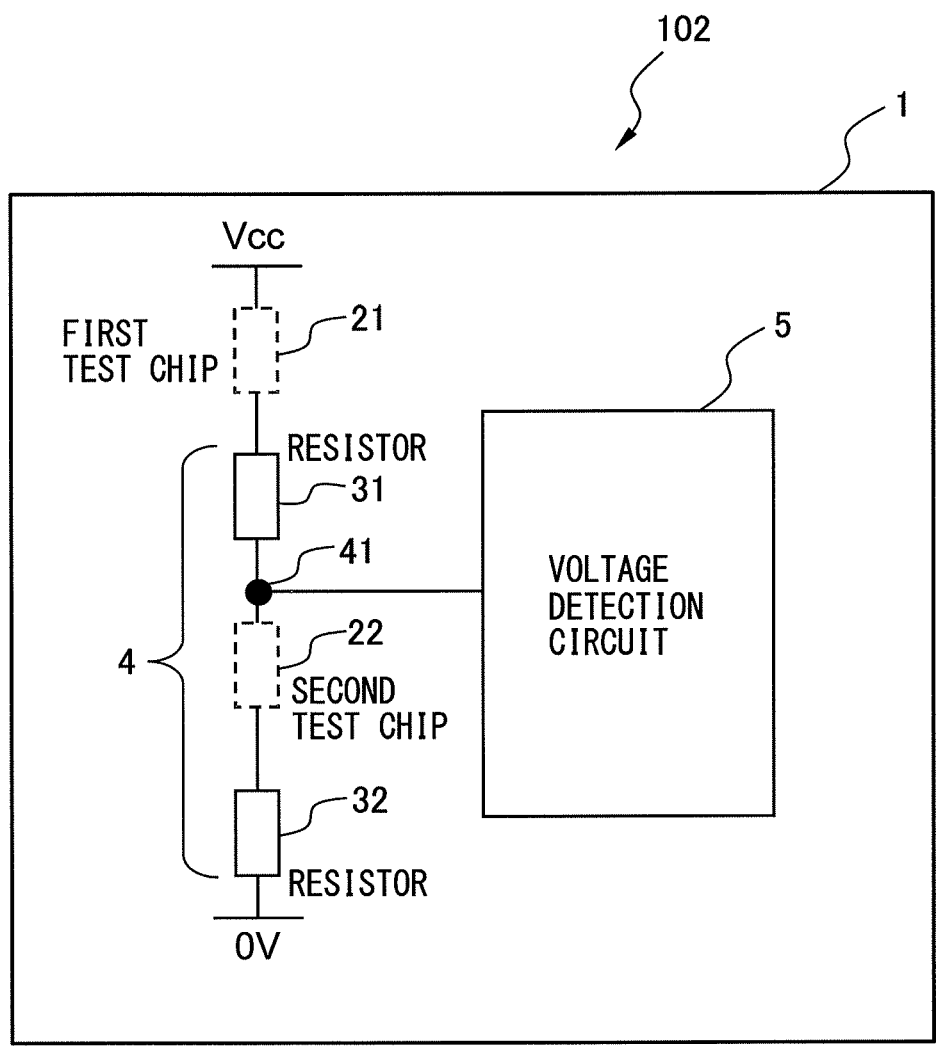
FIG. 7 is a block diagram of a corrosion detection circuit according to a second embodiment of the present invention.

Next, a corrosion detection circuit according to a second embodiment of the present invention will be described. FIG. 7 is a block diagram of the corrosion detection circuit according to the second embodiment of the present invention. The difference between a corrosion detection circuit 102 according to the second embodiment and the corrosion detection circuit 101 according to the first embodiment is that test chips 21 and 22 each having at least one metal different from each other are arranged on the high voltage side and the low voltage side of the divided voltage output point 41 of the voltage dividing circuit 4, respectively. The other configurations of the corrosion detection circuit 102 according to the second embodiment are the same as those of the corrosion detection circuit 101 according to the first embodiment, so a detailed description thereof will be omitted.

The provision of the first test chip 21 and the second test chip 22, which use a plurality of different corrodible metals, on both of the upper and lower sides of the voltage dividing circuit 4, that is, the high voltage side and the low voltage side enables the detection of corrosion due to a plurality of causes. For example, the first test chip 21 may use a corrodible metal of copper, while the second test chip 22 may use a corrodible metal of iron. However, the above is merely an example, and other metals may be used in combination. It is noted that the arrangement of the resistors 31, 32 and the test chips 21 and 22 shown in FIG. 7 is merely an example, and not limited thereto, there is no limitation on the circuit positions of the resistors and the test chips. In other words, the resistors and the test chips may be arranged in a random order from the divided voltage output point 41 of the voltage dividing circuit 4 to the power supply $V_{cc}$ or the ground (0 [V]), between the divided voltage output point 41 and the power supply or between the divided voltage output point 41 and the ground. As examples of a corrosion causative substance, there are halogens such as chlorine and bromine and sulfur. However, not limited to these examples, there are other substances that cause corrosion besides the above-described substances.

Provided that the resistors 31 and 32 each have a resistance value of R, when a voltage $V_{cc}$ is applied to a series circuit including the first test chip 21, the second test chip 22, and the resistors 31 and 32, the voltage of the divided voltage output point 41 is $(\frac{1}{2})V_{cc}$ in a state where neither the first test chip 21 nor the second test chip 22 is broken. At this time, if the first test chip 21 breaks, the voltage of the divided voltage output point 41 becomes 0 [V]. If the second test chip 22 breaks, on the other hand, the voltage of the divided voltage output point 41 becomes $V_{cc}$. Thus, it is possible to detect which of the first test chip 21 and the second test chip 22 has broken from the voltage value of the divided voltage output point 41. For example, in a case where copper is used as the corrodible metal of the first test chip 21 and iron is used as the corrodible metal of the second test chip 22, it is possible to detect which of the metals out of the copper and the iron corrodes from the voltage value of the divided voltage output point 41.

It is noted that, merely as with the corrosion detection circuit 101 according to the first embodiment, in the corrosion detection circuit 102 according to the second embodiment, the first test chip 21 and the second test chip 22 may each include a plurality of test chips connected in series.

As described above, according to the corrosion detection circuit of the second embodiment of the present invention, the additionally provided resistors allow variations in a resistance value of the test chips to be subjected to the corrosion, due to disturbances, other than corrosion to be neglected, thus allowing the stable detection of the corrosion. Furthermore, it is possible to detect the corrosion due to a plurality of causes.

Third Embodiment

Figure 8:
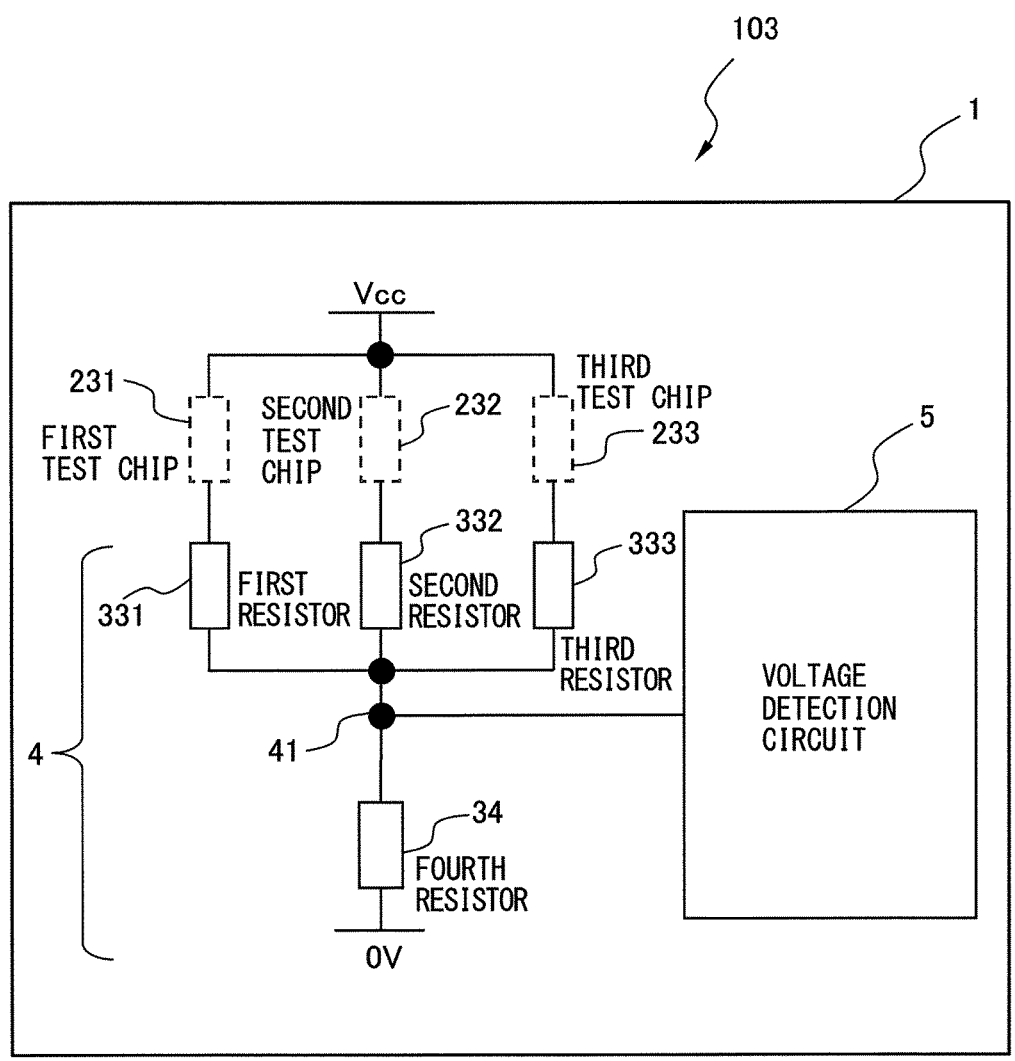
FIG. 8 is a block diagram of a corrosion detection circuit according to a third embodiment of the present invention.

Next, a corrosion detection circuit according to a third embodiment of the present invention will be described. FIG. 8 is a block diagram of the corrosion detection circuit according to the third embodiment of the present invention. The difference between a corrosion detection circuit 103 according to the third embodiment and the corrosion detection circuit 101 according to the first embodiment is that a plurality of pairs of a resistor and a test chip having a different metal are arranged in parallel on at least one of the high voltage side and the low voltage side relative to the divided voltage output point 41 of the voltage dividing circuit 4. The other configurations of the corrosion detection circuit 103 according to the third embodiment are the same as those of the corrosion detection circuit 101 according to the first embodiment, so that a detailed description thereof will be omitted.

In the corrosion detection circuit 103 according to the third embodiment, the plurality of pairs of the resistor and the test chip having the different metal are arranged in parallel on, for example, the high voltage side relative to the divided voltage output point 41. By way of example, as shown in FIG. 8, a series circuit including a first test chip 231 and a first resistor 331, a series circuit including a second test chip 232 and a second resistor 332, and a series circuit including a third test chip 233 and a third resistor 333 are connected in parallel. The first to third test chips 231 to 233 use copper, silver, and iron as the corrodible metals, respectively. However, these are merely examples and other metals may be used instead. It is noted that the arrangement of the resistors and the test chips shown in FIG. 8 is merely an example, and not limited thereto, there is no limitation on the circuit positions of the resistors and the test chips. In other words, the resistors and the test chips are able to be arranged in random order from the divided voltage output point 41 of the voltage dividing circuit 4 to the power supply or the ground, between the divided voltage output point 41 and the power supply or between the divided voltage output point 41 and the ground.

The first to third resistors 331 to 333 each have a resistance value of 6R, and a fourth resistor 34, which is arranged on the low voltage side relative to the divided voltage output point 41, has a resistance value of 2R. When none of the first to third test chips 231 to 233 is broken, the parallel circuit including the first to third resistors 331 to 333 on the high voltage side relative to the divided voltage output point 41 has a resistance value of 2R by the application of a voltage $V_{cc}$, as shown in FIG. 8. Thus, the voltage of the divided voltage output point 41 is $(\frac{1}{2})V_{cc}$.

Next, assume that the corrosion detection circuit 103 has been located in an environment that corrodes the corrodible metal of the first test chip 231, and the first test chip 231 has been broken. At this time, since neither the second test chip 232 nor the third test chip 233 has been broken, the parallel circuit including the second resistor 332 and the third resistor 333 on the high voltage side relative to the divided voltage output point 41 has a resistance value of 3R. Thus, the voltage of the divided voltage output point 41 is $(2/3)V_{cc}$.

Next, assume that the corrosion detection circuit 103 has been further located in an environment that corrodes the corrodible metal of the second test chip 232, and the second test chip 232 has been broken in addition to the first test chip 231. At this time, since the third test chip 233 has not been broken, the high voltage side relative to the divided voltage output point 41 has a resistance value of 6R. Thus, the voltage of the divided voltage output point 41 is $(1/4)V_{cc}$.

Next, assume that the corrosion detection circuit 103 has been further located in an environment that corrodes the corrodible metal of the third test chip 233, and all of the first to third test chips 231 to 233 have been broken. At this time, the voltage of the divided voltage output point 41 becomes 0 [V].

Although the above describes an example in which the plurality of pairs of the resistor and the test chip having different metals are arranged in parallel on the high voltage side relative to the divided voltage output point 41 of the voltage dividing circuit 4, the present invention is not limited thereto. That is, the plurality of pairs of the resistor and the test chip having different metals may be arranged in parallel on the low voltage side relative to the divided voltage output point 41 of the voltage dividing circuit 4, or on both of the high voltage side and the low voltage side.

Furthermore, the above-described resistance values of the first to third resistors 331 to 333 are merely examples, and may be varied. By setting the resistance values of the first to third resistors 331 to 333 at different values from each other, it is possible to detect which of the first to third test chips 231 to 233 has been broken.

Also, the three series circuits i.e. the three pairs of the test chip and the resistor are arranged in parallel in the above description, but the number of the series circuits may be two or four or more. Furthermore, each test chip may include a plurality of test chips connected in series.

As described above, according to the corrosion detection circuit 103 of the third embodiment of the present invention, it is possible to detect corrosion due to a plurality of corrosion causes from a detection result of the voltage of the divided voltage output point 41.

Fourth Embodiment

Figure 9:
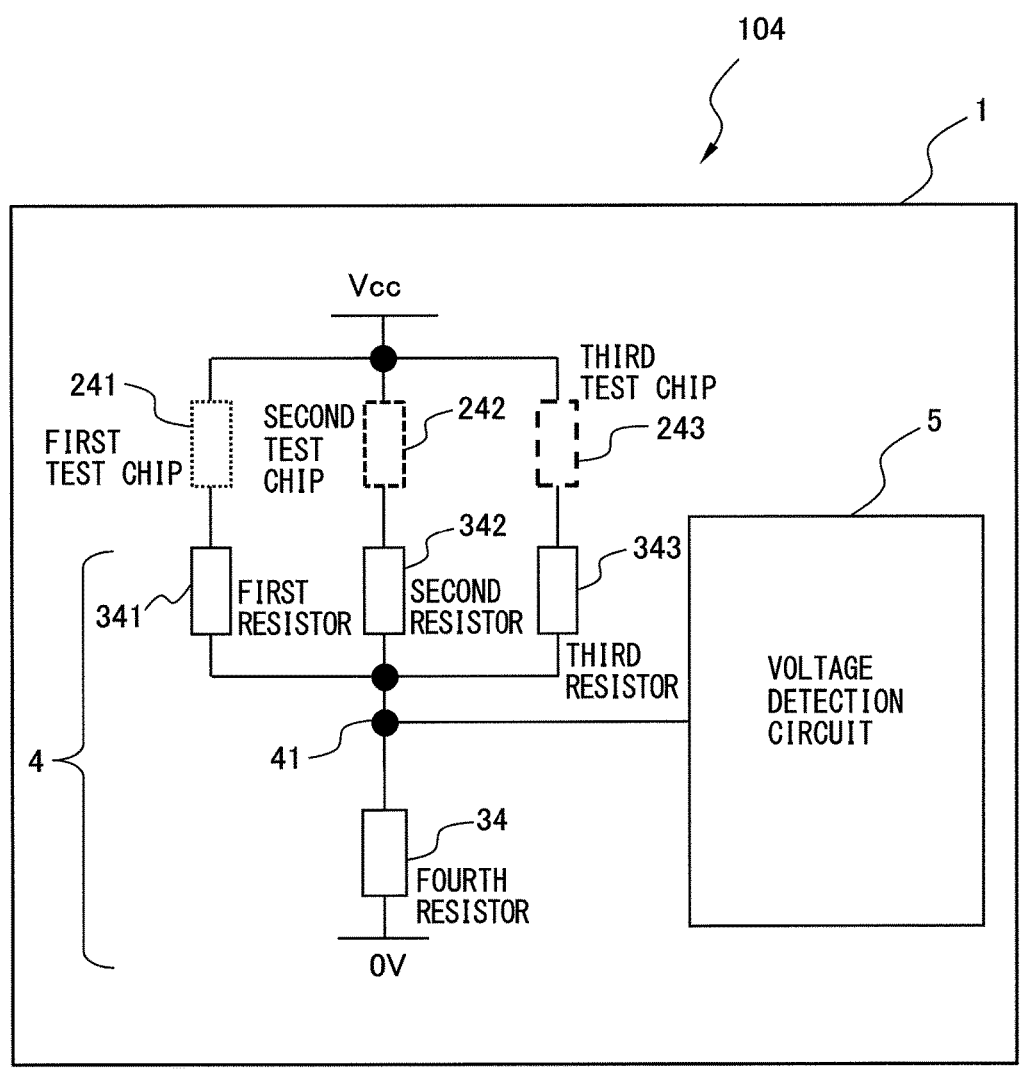
FIG. 9 is a block diagram of a corrosion detection circuit according to a fourth embodiment of the present invention.

Next, a corrosion detection circuit according to a fourth embodiment of the present invention will be described. FIG. 9 is a block diagram of the corrosion detection circuit according to the fourth embodiment of the present invention. The difference between a corrosion detection circuit 104 according to the fourth embodiment and the corrosion detection circuit 101 according to the first embodiment is that a plurality of pairs of a resistor and a test chip that has the same metal having a different corrosion resistance are arranged in parallel on at least one of the high voltage side and the low voltage side relative to the divided voltage output point 41 of the voltage dividing circuit 4. The other configurations of the corrosion detection circuit 104 according to the fourth embodiment are the same as those of the corrosion detection circuit 101 according to the first embodiment, so that a detailed description thereof will be omitted.

In the corrosion detection circuit 104 according to the fourth embodiment, the plurality of pairs of the resistor and the test chip that has the same metal having the different corrosion resistance are arranged in parallel on, for example, the high voltage side relative to the divided voltage output point 41. By way of example, as shown in FIG. 9, a series circuit including a first test chip 241 and a first resistor 341, a series circuit including a second test chip 242 and a second resistor 342, and a series circuit including a third test chip 243 and a third resistor 343 are connected in parallel. The first to third test chips 241 to 243 use a corrodible metal having different resistances to corrosion (corrosion resistances). As an example, the first test chip 241 may be the most susceptible to corrosion, the second test chip 242 may be the second most susceptible to corrosion, and the third test chip 243 may be the least susceptible to corrosion. As the corrodible metal, the same metal e.g. copper may be used. However, this is merely an example and another metal such as silver or iron may be used instead. It is noted that the arrangement of the resistors and the test chips shown in FIG. 9 is merely an example, and not limited thereto, there is no limitation on the circuit positions of the resistors and the test chips. In other words, the resistors and the test chips may be arranged in a random order from the divided voltage output point 41 of the voltage dividing circuit 4 to the power supply ($V_{cc}$) or the ground (0 [V]), between the divided voltage output point 41 and the power supply or between the divided voltage output point 41 and the ground.

The first to third resistors 341 to 343 each have a resistance value of 6R, and a fourth resistor 34, which is arranged on the low voltage side relative to the divided voltage output point 41, has a resistance value of 2R. When none of the first to third test chips 241 to 243 is broken, the parallel circuit including the first to third resistors 341 to 343 on the high voltage side relative to the divided voltage output point 41 has a resistance value of 2R by the application of a voltage $V_{cc}$, as shown in FIG. 9. Thus, the voltage of the divided voltage output point 41 is $(1/2)V_{cc}$.

Figure 10:
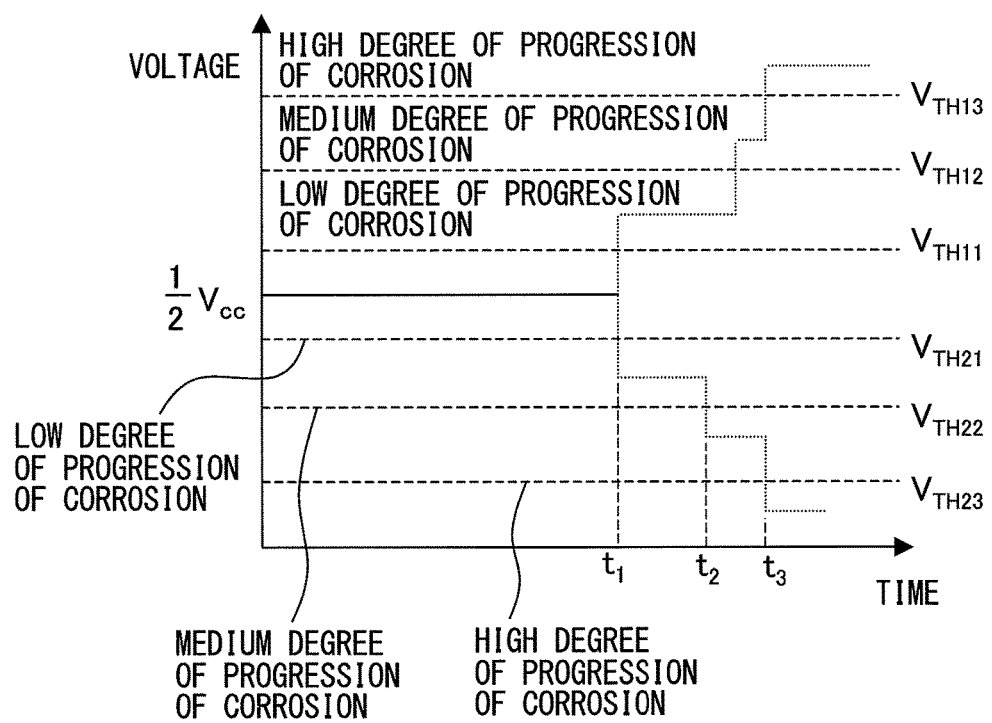
FIG. 10 is a graph showing variations in the output of a voltage dividing circuit in the corrosion detection circuit according to the fourth embodiment of the present invention.

FIG. 10 shows temporal variations in the output of the voltage dividing circuit in the corrosion detection circuit according to the fourth embodiment of the present invention. When the first test chip 241 that is the most susceptible to corrosion is broken at a time $t_1$, the voltage of the divided voltage output point 41 is $(1/2)V_{cc}$ before the time $t_1$.

Next, assume that the corrosion detection circuit 104 has been located in an environment that corrodes the corrodible metal of the first test chip 241, which is the most susceptible to corrosion, and the first test chip 241 has been broken at the time $t_1$. At this time, since neither the second test chip 242 nor the third test chip 243 has been broken, the parallel circuit including the second resistor 342 and the third resistor 343 on the high voltage side relative to the divided voltage output point 41 has a resistance value of 3R. Thus, the voltage of the divided voltage output point 41 is $(2/3)V_{cc}$.

By determining a first threshold $V_{TH21}$ at a value between $(1/2)V_{cc}$ and $(2/3)V_{cc}$, it is possible to detect that the corrodible metal that is the most susceptible to corrosion has corroded (a low degree of the progression of corrosion), based on the fact that the voltage of the divided voltage output point 41 has fallen below the first threshold $V_{TH21}$.

Next, assume that the corrosion detection circuit 104 has been further located in an environment that corrodes the corrodible metal of the second test chip 242, which is the second most susceptible to corrosion, and the second test chip 242 has been broken at a time $t_2$ in addition to the first test chip 241. At this time, since the third test chip 243 has not been broken, the high voltage side relative to the divided voltage output point 41 has a resistance value of 6R. Thus, the voltage of the divided voltage output point 41 is (¼)$V_{cc}$.

By determining a second threshold $V_{TH22}$ at a value between (⅖)$V_{cc}$ and (¼)$V_{cc}$, it is possible to detect that the corrodible metal that is the second most susceptible to corrosion has corroded (a medium degree of the progression of corrosion), based on the fact that the voltage of the divided voltage output point 41 has fallen below the second threshold $V_{TH22}$.

Next, assume that the corrosion detection circuit 104 has been further located in an environment that corrodes the corrodible metal of the third test chip 243, which is the least susceptible to corrosion, and all of the first to third test chips 241 to 243 have been broken. At this time, the voltage of the divided voltage output point 41 becomes 0 [V].

By determining a third threshold $V_{TH23}$ at a value between (¼)$V_{cc}$ and 0 [V], it is possible to detect that the corrodible metal that is the least susceptible to corrosion has corroded (a high degree of the progression of corrosion), based on the fact that the voltage of the divided voltage output point 41 has fallen below the third threshold $V_{TH23}$.

The above-described resistance values of the first to third resistors 341 to 343 are merely examples and may be varied.

Also, the three series circuits, that is, the three pairs of the test chip and the resistor are arranged in parallel in the above description, but the number of the series circuits may be two or four or more. Furthermore, each test chip may include a plurality of test chips connected in series.

Although the above describes an example in which the plurality of pairs of the resistor and the test chip that have the same metal having the different corrosion resistance are arranged in parallel on the high voltage side relative to the divided voltage output point 41 of the voltage dividing circuit 4, the present invention is not limited thereto. That is, the plurality of pairs of the resistor and the test chip that have the same metal having different corrosion resistances may be arranged in parallel on the low voltage side relative to the divided voltage output point 41 of the voltage dividing circuit 4, or on both of the high voltage side and the low voltage side.

For example, when the plurality of pairs of the resistor and the test chip that have the same metal having different corrosion resistances are arranged in parallel on the low voltage side relative to the divided voltage output point 41 of the voltage dividing circuit 4, the voltage of the divided voltage output point 41 increases stepwise with the breakage of the first to third test chips. Appropriately setting first to third threshold voltages $V_{TH11}$ to $V_{TH13}$ allows detecting which of the first to third test chips has been broken.

As described above, according to the corrosion detection circuit of the fourth embodiment of the present invention, the plurality of test chips having different resistances to corrosion are used. Since the test chips are broken in decreasing order of susceptibility to corrosion, the stepwise voltage variation serves to detect the degree of the progression of corrosion.

Fifth Embodiment

Figure 11:
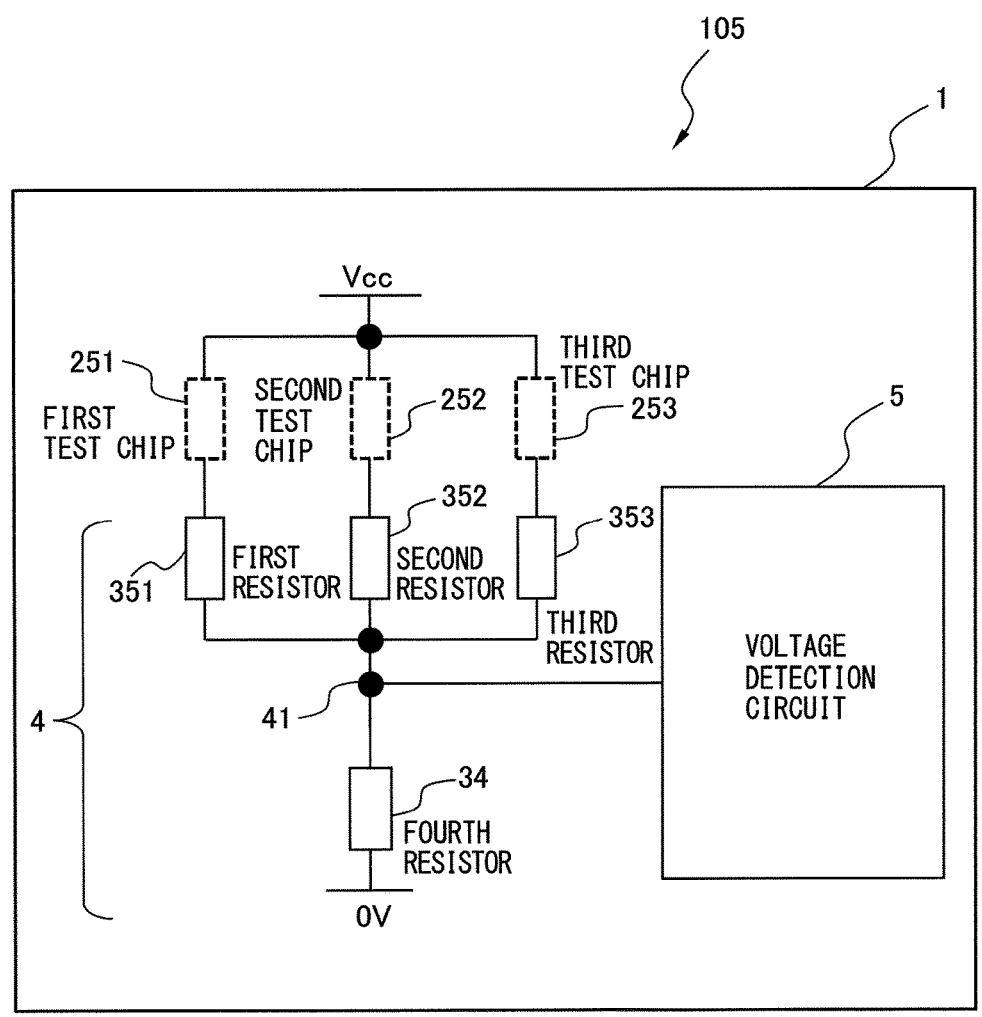
FIG. 11 is a block diagram of a corrosion detection circuit according to a fifth embodiment of the present invention.

Next, a corrosion detection circuit according to a fifth embodiment of the present invention will be described. FIG. 11 is a block diagram of the corrosion detection circuit according to the fifth embodiment of the present invention. The difference of a corrosion detection circuit 105 according to the fifth embodiment from the corrosion detection circuit 101 according to the first embodiment is that a plurality of pairs of a resistor and an identical test chip are arranged in parallel on at least one of the high voltage side and the low voltage side relative to the divided voltage output point 41 of the voltage dividing circuit 4. The other configurations of the corrosion detection circuit 105 according to the fifth embodiment are the same as those of the corrosion detection circuit 101 according to the first embodiment, so that a detailed description thereof will be omitted.

In the corrosion detection circuit 105 according to the fifth embodiment, the plurality of pairs of the resistor and the identical test chip are arranged in parallel on, for example, the high voltage side relative to the divided voltage output point 41. By way of example, as shown in FIG. 11, a series circuit including a first test chip 251 and a first resistor 351, a series circuit including a second test chip 252 and a second resistor 352, and a series circuit including a third test chip 253 and a third resistor 353 are connected in parallel. The first to third test chips 251 to 253 are identical. As an example, the same metal e.g. copper may be used as the corrodible metal. However, this is merely an example and another metal such as silver or iron may be used instead. It is noted that the arrangement of the resistors and the test chips shown in FIG. 11 is merely an example, and not limited thereto, there is no limitation on the circuit positions of the resistors and the test chips. In other words, the resistors and the test chips may be arranged in a random order from the divided voltage output point 41 of the voltage dividing circuit 4 to the power supply ($V_{cc}$) or the ground (0 [V]), between the divided voltage output point 41 and the power supply or between the divided voltage output point 41 and the ground.

Figure 12:
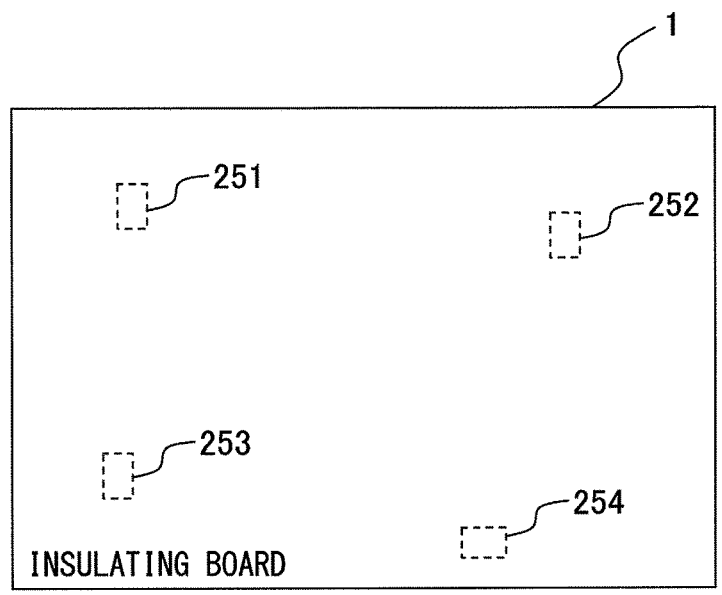
FIG. 12 is a plan view showing an example in which test chips of the corrosion detection circuit according to the fifth embodiment of the present invention are arranged in a plurality of positions on an insulating board.

FIG. 12 shows an example in which the test chips of the corrosion detection circuit according to the fifth embodiment of the present invention are mounted in a plurality of positions on an insulating board. The first to fourth test chips 251 to 254 are identical, and may be mounted in the plurality of positions on the insulating board 1. The arrangement of the test chips 251 to 254 in the various positions on the insulating board 1 facilitates detecting corrosion in a wide area. FIG. 12 omits the resistors, but the resistors may be arranged in the vicinity of the test chips or at a distance from the test chips. By varying the resistance values of the resistors 351 to 353, it is possible to detect which of the test chips has been broken from the value of the divided voltage output point 41.

As described above, according to the corrosion detection circuit of the fifth embodiment of the present invention, it is possible to detect corrosion in the wide area of the insulating board.

Sixth Embodiment

Figure 13:
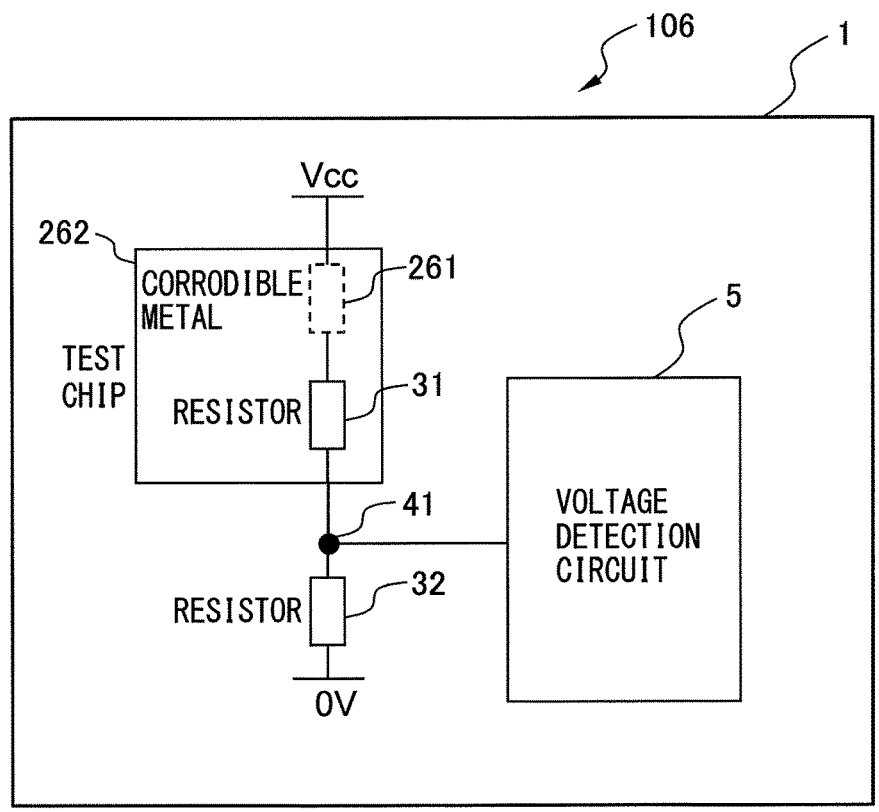
FIG. 13 is a block diagram of a corrosion detection circuit according to a sixth embodiment of the present invention.

Next, a corrosion detection circuit according to a sixth embodiment of the present invention will be described. FIG. 13 is a block diagram of the corrosion detection circuit according to the sixth embodiment of the present invention. The difference between a corrosion detection circuit 106 according to the sixth embodiment and the corrosion detection circuit 101 according to the first embodiment is that a corrodible metal 261 and a resistor 31 are integrated into a test chip 262. The other configurations of the corrosion detection circuit 106 according to the sixth embodiment are the same as those of the corrosion detection circuit 101 according to the first embodiment, so a detailed description thereof will be omitted.

In the corrosion detection circuit 106 according to the sixth embodiment, an integrated unit of the resistor 31 and the corrodible metal 261 is mounted on the insulating board 1 as the test chip 262. Thus, it is possible to reduce mounting space and cost.

The above describes discrete corrosion detection circuits, but the above-described corrosion detection circuits may be used in circuit boards for motor drives.

According to the corrosion detection circuits of the embodiments of the present invention, since the voltage dividing circuit is provided with the resistors that each have a much higher resistance value than the test chip after a change due to an environmental factor such as contact with the test chip and the adhesion of dust to the test chip, it is possible to neglect variations in the resistance value of the test chip and detect corrosion in a stable manner.

The resistors and the test chip are mounted by soldering at the same time as soldering of other components, so that the present invention is easily realized without an increase in the number of processing steps. The resistors can be inexpensive general resistors, thus reducing cost.

What is claimed is:

1. A corrosion detection circuit comprising:
    an insulating board;
    a first test chip having a corrodible metal mounted on the surface of the insulating board;
    at least a first resistor and a second resistor, and a divided voltage output located between the first and second resistor, the divided voltage output having a high side and a low side, each of the first and second resistors having a higher resistance value than the first test chip after a change due to an environmental factor including contact with the test chip and an adhesion of dust to the first test chip; and
    a voltage detection circuit for detecting the output voltage of the divided voltage output point, when a voltage is applied to the corrosion detection circuit,
wherein the first and second resistors are connected in series with the first test chip, and
    wherein, if the first test chip is located on the high voltage side of the divided voltage output point of the divided voltage circuit, the voltage detection circuit detects a break in the first test chip by corrosion when the voltage of the divided voltage output point decreases from a voltage depending on the plurality of resistors and falls below a first threshold; and
    wherein, if the first test chip is located on the low voltage side of the divided voltage output point of the divided voltage circuit, the voltage detection circuit detects a break in the first test chip by corrosion when the voltage of the divided voltage output point increases from the voltage depending on the plurality of resistors and exceeds a second threshold.

2. The corrosion detection circuit according to claim 1 further comprising at least one second test chip, wherein the first test chip has at least one metal different from the at least one second test chip and the first test chip is arranged on the high voltage side of the voltage detection circuit and the at least one second test chip is arranged on the low voltage side relative to the divided voltage output point of the voltage dividing circuit.

3. The corrosion detection circuit according to claim 1, further comprising a plurality of pairs of a resistor and an additional test chip arranged in parallel on at least one of the high voltage side and the low voltage side of the voltage dividing circuit, wherein the additional test chip is made of a different metal than the first test chip.

4. The corrosion detection circuit according to claim 1, further comprising a plurality of pairs of a resistor and an additional test chip arranged in parallel on at least one of the high voltage side and the low voltage side of the voltage dividing circuit, wherein the additional test chip is made of the same metal as the first test chip.

5. The corrosion detection circuit according to claim 1, further comprising a plurality of pairs of a resistor and an additional test chip arranged in parallel on at least one of the high voltage side and the low voltage side of the voltage dividing circuit.

6. The corrosion detection circuit according to claim 1, wherein the corrodible metal and the first resistor are integrated into the test chip.

7. A motor drive comprising the corrosion detection circuit according to claim 1.